United States Patent [19]

Tsuru et al.

[11] Patent Number: 4,687,778
[45] Date of Patent: Aug. 18, 1987

[54] ANTI-AMNESTIC AGENT

[75] Inventors: Daisuke Tsuru; Tadashi Yoshimoto, both of Nagasaki; Hisao Hagiwara; Kunio Kado, both of Tokyo, all of Japan

[73] Assignee: Kabushiki Kaisha Yakult Honsha, Tokyo, Japan

[21] Appl. No.: 709,682

[22] Filed: Mar. 8, 1985

[30] Foreign Application Priority Data

Mar. 9, 1984 [JP] Japan .................................. 59-43751

[51] Int. Cl.⁴ ............................................. A61K 31/40
[52] U.S. Cl. .................................................. 514/419
[58] Field of Search ........................ 514/419, 422, 423

[56] References Cited

PUBLICATIONS

Chem. Abst. 99, 101,433f, (1983).

Primary Examiner—Stanley J. Friedman
Attorney, Agent, or Firm—Birch, Stewart, Kolasch & Birch

[57] ABSTRACT

An anti-amnestic agent which comprises as an active ingredient thereof at least one prolinal derivative of the general formula:

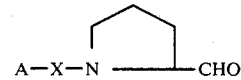

wherein A is a protective groups for amino group in the field of amino acid chemistry and X is a residue of an amino acid, in a pharmacologically active amount together with an exipient. This agent is less toxic and can be safely administered to patients orally or intravenously for the remedy of memory disorder.

6 Claims, No Drawings

ANTI-AMNESTIC AGENT

BACKGROUND OF THE INVENTION

1. Field of the Invention

The present invention relates to a new type anti-amnestic agent. More particularly, the present invention relates to a new type anti-amnestic agent containing a specific prolinal derivative as an active ingredient thereof.

2. Description of the Prior Art

In recent years, it has been made clear that vasopressin, oxytocin and the like peptide hormones participate in memory. B. Bohus et al. report that the administration of such peptide hormones to experimentally made amnestic rats showed obvious recovery of memory [Béla Bohus et al., Brain Research 157 (1978) 414–417]. It is also reported that such peptide hormones showed a similar effect in clinical tests for human [H. Weingartner et al., Science 211, (1981), 601–603]. It is known that all of these peptide hormones contain proline and exist in brain. These peptide hormons are anticipated to be metabolized with internal peptidase among which proline-specific endopeptidase (post-proline cleaving enzyme) are supposed because of their specific nature to participate in the metabolism of many proline-containing peptide hormons.

Various approaches have been made from the past to proline-specific endopeptidase inhibitory agents. Among these approaches, a special concern is paid to the fact that N-benzyloxycarbonylglycyl-L-prolyl-chloromethane and N-benzyloxycarbonyl-L-prolyl-prolinal possess a strong inhibitory action to the endopeptidase [T. Yoshimoto et al., Biochem. 16 (1977), 2942-2948 and S. Sherwin et al, Neurochem. Wilk et al., J. Neurochem. 41 (1983), 69–75]. In this aspect, therefore, further approach is demanded to study biochemical activities of such endopeptidase inhibitory agents.

BRIEF SUMMARY OF THE INVENTION

As a result of extensive researches made on the endopeptidase inhibitory substances, it has now been found unexpectedly that a prolinal derivative of the general formula

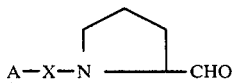

wherein A is a protective group for amino group in the field of amino acid chemistry and X is a residue of an amino acid, possesses a strong anti-amnestic action.

Accordingly, it is an object of the present invention to provide new prolinal derivatives possessing valuable pharmacological properties.

It is another object of the present invention to provide a new type anti-amnestic agent comprising at least one of the prolinal derivative as an active ingredient thereof.

It is still another object of the present invention to provide a method for using the new type anti-amnestic agent for the remedy of memory disorder.

Other objects, features and advantages of the present invention will be apparent more fully from the following description.

DETAILED DESCRIPTION OF THE INVENTION

In accordance with the present invention, there is provided an anti-amnestic agent which comprises as an active ingredient thereof at least one prolinal derivative of the general formula:

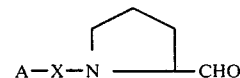

wherein A is a protective group for amino groups in the field of amino acid chemistry and X is a residue of an amino acid, in a pharmacologically active amount together with a conventional excipient.

The fact that a prolinal derivative represented by the above general formula exhibits a strong anti-amnestic activity has for the first time been found by the present inventors. The present invention has been accomplished on the basis of the above finding.

As a result of the present inventors' thorough investigation of the effect of the prolinal derivatives of the general formula on the study of a passive avoidance of rats, it has been made clear that these prolinal derivatives exhibit an extremely strong anti-amnestic activity by oral or intraperitoneal administration and are less toxic physiologically safe substances so that they can be utilized, for example, as a drug for dementia senilis of the Alzheimer's type.

The majority of the prolinal derivatives of the general formula are new substances but can be prepared according to a method known per se in amino acid chemistry. For example, an amino-protected amino acid is reacted with N-hydroxysuccinimide and a carbodiimide such as dicyclohexylcarbodiimide under cooling and then with L-prolinol to form an oily or solid product which is then treated with 1-(3-dimethylaminopropyl)-3-ethyl carbodiimide. In this case, a protective group A for the amino group of an amino acid corresponding to X is known in the field of amino acid chemistry and is usually selected from N-benzyloxycarbonyl group, t-butyloxycarbonyl group and a lower acyl group with 2-4 carbon atoms such as an acetyl group.

The prolinal derivatives of the general formula can be administered to patients in various ways such as injection, for example, intravenous, subcutaneous or intramuscular injection and chewable or drinkable preparations suitable for oral administration. Normally, the prolinal derivatives are used singly or may be used as a mixture of at least two. Further, the prolinal derivatives are normally blended with a suitable excipient usually employed for pharmaceutical formulations. An excipient utilizable for this purpose includes one or more organic and inorganic substances which are suitable for enteral or parenteral administration and do not react with the prolinal derivatives of the general formula, for example, water, vegetable oils, benzyl alcohol, polyethylene glycols, gelatin, carbohydrates such as lactose and starch, magnesium stearate, talc or white petroleum jelly. Other organic and inorganic substances usually employed for preparing various medicaments can also be used as the excipient unless they do not influence the effect of the prolinal derivatives. The formulations used for oral administration must easily be absorbed in digestive organs and are, in particular, powders, tablets, pills, dragees, hard and soft capsules, syrups, juices, drops, elixirs and other orally acceptable liquid preparations, preferably oily or aqueous solutions, suspensions and emulsions. The formulations for various types of injection preparations are as a rule in the form of the above liquid preparations. For injection, the prolinal derivatives may be lyophilized and the resulting lyophilizate may be used at need for such injection preparations. The indicated formulations can be sterilized and/or contain one or more auxiliary substances such as lubricants, preservatives, stabilizers and/or wetting agents, emulsifiers, salts for influencing the osmotic pressure, buffer substances, dyestuffs, flavoring agents and/or aroma substances. They can also contain, if desired, one or more further active compounds, for example, lecithin, one or more vitamins, and depressants.

The invention also relates to the use of the prolinal derivatives of the general formula for the remedy of memory disorder of human, for example, dementia senilis of the Alzheimer's.

Particularly preferable as a mode of administration of the prolinal derivatives are oral administration and intravenous injection. The daily dose of the prolinal derivatives is preferably between 1 mg and 900 mg/Kg, especially between 5 mg and 500 mg/Kg of body weight in case of oral administration and between 0.5 mg and 500 mg/Kg, especially between 1 mg and 200 mg/Kg of body weight in case of intravenous injection. The particular dose for each specific patient depends, however, on very diverse factors, for example, the effectiveness of the particular prolinal derivative employed, the age, the body weight, the general state of health and the sex, the diet, the time and mode of administration, the rate of elimination, the combination of medicaments and the severity of the particular ailment to which the remedy applies. In the anti-amnestic agents of the present invention, the prolinal derivative or derivatives as active ingredient are contained generally in a concentration of 0.1% or more, preferably 1–50% by weight.

Described below are the anti-amnestic action and toxicity of the prolinal derivatives of the above general formula confirmed by the present inventors.

1. Anti-amnestic action

The method of assay of the anti-amnestic action was carried out according to the method reported by A. Kubota et al. in Int. Symp. on the Pharmacology of Learning and Memory, at Hakone, Japan (July 25, 1981) to measure the effect of the prolinal derivatives on passive avoidance response of rats. A passive avoidance chamber used in this test was surrounded with inside-visible transparent plastic plates and included an electrifiable grid floor (30 cm in length and 30 cm in width) capable of being derivered with an electric current of 1.7 mA in strength for electric foot shock and a platform (15 cm in length, 15 cm in width and 4 cm in height) placed at the right back corner thereof. A male Wister SLC rat (weighing 100–150 g) was placed in the passive avoidance chamber and, when he stepped down on the floor, the electric current was sent to the grid continuously until he went up on the platform. Repeating this test with another rat, the rats stayed on the platform for more than 15 seconds were taken out of the chamber, being regarded to have learned the situation. This electric shock was normally 2 or 3 times. To avoid any difference in the rats, those required 10 seconds for the first step-down and those stepped down on the floor at least 5 times were excluded. Among the learned or trained rats, the first control group of them were intraperitoneally administered with 0.5% CMC solution and the other groups of them were intraperitoneally administered with scopolamine hydrobromide in a dose of 3 mg/Kg to prepare experimental amnestic rats. The prolinal derivatives of the general formula to be tested were in each case intraperitoneally or orally administered to the rats in an amount shown in Table 1 or 2 one after completion of the learning. In each case, the polinal derivatives are used as having been dissolved or suspended in a 0.5% CMC solution. Results of the tests are shown in Tables 1 and 2. The prolinal derivatives showed a significant extension of the latency time in intraperitoneal and oral administration as compared with the control.

2. Toxicity test

Using 4-weeks-old male ICR mice weighing 15–20 g, the value of $LD_{50}$ was calculated by orally or intraperitoneally administering the prolinal derivatives to the mice and counting the deceased mice according to the conventional method. A result of this toxicity test is shown in Table 3.

In view of the results shown in Tables 1–3, it is evident that the prolinal derivatives of the general formula possess excellent anti-amnestic action with slight toxicity and are thus widely utilizable for the remedy of memory disorder such as dementia senilis of the Alzheimer's type.

Throughout the specification, the percentage is by weight unless otherwise indicated.

TABLE 1

Effects of various Prolinal Derivatives on Amnesia (i.p.)

| Agent used | Amount administered (mg/kg) | Administration Route | Treatment after Training | Training Step down Latency (sec) | Number of Descending within the Training (times) | Total Time required for Test (sec) | Retention Test Latency (sec) 24 hr | Retention Test Latency (sec) 48 hr | Number of Animals used |
|---|---|---|---|---|---|---|---|---|---|
| 0.5% CMC (Control) | — | i.p. | 0.5% CMC | 2.0 | 1.2 | 29.8 | 181.0 | 180.6 | 5 |
| 0.5% CMC (Control) | — | i.p. | Scopolamine | 2.4 | 1.8 | 30.6 | 117.4 | 106.2 | 5 |
| N—Benzyloxycarbonyl-glycyl-prolinal | 1.9 | i.p. | Scopolamine | 2.2 | 1.6 | 50.8 | >300.0 | >300.0 | 5 |
| N—Benzyloxycarbonyl-alanyl-prolinal | 2.0 | i.p. | Scopolamine | 1.8 | 1.0 | 35.8 | 189.0 | 203.4 | 5 |
| N—Benzyloxycarbonyl-valyl-prolinal | 2.2 | i.p. | Scopolamine | 1.2 | 2.4 | 28.2 | >300.0 | >300.0 | 5 |
| N—Benzyloxycarbonyl-prolyl-prolinal | 2.2 | i.p. | Scopolamine | 6.7 | 1.3 | 39.5 | 192.0 | 141.5 | 4 |
| N—Benzyloxycarbonyl-leucyl-prolinal | 3.5 | i.p. | Scopolamine | 2.3 | 1.4 | 38.5 | >300.0 | >300.0 | 5 |
| t-Butyloxycarbonyl- | 1.8 | i.p. | Scopolamine | 1.9 | 1.5 | 28.5 | 293.5 | 250.4 | 5 |

TABLE 1-continued

Effects of various Prolinal Derivatives on Amnesia (i.p.)

| Agent used | Amount administered (mg/kg) | Administration Route | Treatment after Training | Step down Latency (sec) | Number of Descending within the Training (times) | Total Time required for Test (sec) | Retention Test Latency (sec) 24 hr | Retention Test Latency (sec) 48 hr | Number of Animals used |
|---|---|---|---|---|---|---|---|---|---|
| alanyl-prolinal | | | | | | | | | |
| t-Butyloxycarbonyl-phenylalanyl-prolinal | 3.0 | i.p. | Scopolamine | 2.0 | 2.0 | 32.3 | >300.0 | 264.3 | 5 |
| t-Butyloxycarbonyl-seryl-prolinal | 2.9 | i.p. | Scopolamine | 1.8 | 1.9 | 39.6 | >300.0 | >300.0 | 5 |
| t-Butyloxycarbonyl-tyrosyl-prolinal | 3.6 | i.p. | Scopolamine | 2.2 | 1.4 | 34.7 | 250.8 | 206.9 | 4 |
| Acetyl-glycl-prolinal | 1.3 | i.p. | Scopolamine | 2.3 | 1.4 | 30.0 | 274.9 | 198.6 | 5 |
| Acetyl-prolyl-prolinal | 2.3 | i.p. | Scopolamine | 1.9 | 1.5 | 41.3 | >300.0 | >300.0 | 4 |

Remarks: In each case scopolamine in an amount of 3 mg/kg was intraperitoneally administered.

TABLE 2

Effects of various Prolinal Derivatives on Amnesia (p.o.)

| Agent used | Amount administered (mg/kg) | Administration route | Treatment after Training | Step down Latency (sec) | Number of Descending within the Training (times) | Total Time required for Test (sec) | Retention Test Latency (sec) 24 hr | Retention Test Latency (sec) 48 hr | Number of Animals used |
|---|---|---|---|---|---|---|---|---|---|
| 0.5% CMC (Control) | — | p.o. | 0.5% CMC | 2.2 | 1.7 | 29.7 | 260.7 | 204.8 | 5 |
| 0.5% CMC (Control) | — | p.o. | Scopolamine | 6.9 | 2.6 | 52.4 | 121.7 | 80.5 | 6 |
| N—Benzyloxycarbonyl-glycyl-prolinal | 1.9 | p.o. | Scopolamine | 4.0 | 2.5 | 49.2 | 230.4 | 175.5 | 5 |
| N—Benzyloxycarbonyl-alanyl-prolinal | 2.0 | p.o. | Scopolamine | 3.5 | 1.8 | 36.5 | 165.4 | 155.2 | 5 |
| N—Benzyloxycarbonyl-valyl-prolinal | 2.2 | p.o. | Scopolamine | 2.8 | 2.4 | 32.0 | 254.8 | 210.5 | 6 |
| N—Benzyloxycarbonyl-prolyl-prolinal | 2.2 | p.o. | Scopolamine | 3.9 | 1.3 | 36.5 | 140.2 | 102.3 | 5 |
| N—Benzyloxycarbonyl-leucyl-prolinal | 3.5 | p.o. | Scopolamine | 2.3 | 1.6 | 32.1 | 281.6 | 219.5 | 5 |
| t-Butyloxycarbonyl-alanyl-prolinal | 1.8 | p.o. | Scopolamine | 4.3 | 2.1 | 52.4 | 239.8 | 226.7 | 5 |
| t-Butyloxycarbonyl-phenylalanyl-prolinal | 3.0 | p.o. | Scopolamine | 5.6 | 2.0 | 47.1 | >300.0 | 250.2 | 4 |
| t-Butyloxycarbonyl-seryl-prolinal | 2.9 | p.o. | Scopolamine | 2.9 | 1.9 | 45.2 | 262.9 | 185.2 | 5 |
| t-Butyloxycarbonyl-tyrosyl-prolinal | 3.6 | p.o. | Scopolamine | 4.3 | 1.8 | 32.5 | 180.5 | 192.1 | 5 |
| Acetyl-glycyl-prolinal | 1.3 | p.o. | Scopolamine | 3.3 | 1.5 | 35.5 | 221.6 | 143.2 | 5 |
| Acetyl-prolyl-prolinal | 2.3 | p.o. | Scopolamine | 1.9 | 1.4 | 40.3 | 204.2 | 177.4 | 5 |

Remarks: In each case scopolamine in an amount of 3 mg/kg was intraperitoneally administered.

TABLE 3

LD$_{50}$(ip) Values of various Prolinal Derivatives

| Prolinal Derivatives | LD$_{50}$ (mg/kg) |
|---|---|
| N—Benzyloxycarbonyl-glycyl-prolinal | >1,000 |
| N—Benzyloxycarbonyl-alanyl-prolinal | 954 |
| N—Benzyloxycarbonyl-valyl-prolinal | 825 |
| N—Benzyloxycarbonyl-prolyl-prolinal | >1,000 |
| N—Benzyloxycarbonyl-leucyl-prolinal | >1,000 |
| t-Butyloxycarbonyl-alanyl-prolinal | 796 |
| t-Butyloxycarbonyl-phenylalanyl-prolinal | >1,000 |
| t-Butyloxycarbonyl-seryl-prolinal | >1,000 |
| t-Butyloxycarbonyl-tyrosyl-prolinal | 933 |
| Acetyl-glycyl-prolinal | >1,000 |
| Acetyl-prolyl-prolinal | 767 |

Animals used: ICR male mice

The following examples illustrate the preparation of the various prolinal derivatives of the general formula given above as effective ingredients of the anti-amnestic agents of the present invention wherein all the amino acids except glycin were used in L-form. In these Examples the abbreviations used for the amino acid residues are as follows:

| Ala | alanine | Val | valine |
|---|---|---|---|
| Gly | glycine | Leu | leucine |
| Phe | phenylalanine | Ser | Serine |
| Pro | Proline | Tyr | tyrosine |

Likewise, the abbreviations used for the compounds and for the protecting groups present in the amino group of the amino acid structure are as follows:

| DCC | dichlorohexylcarbodiimide |
|---|---|
| WSCD.HCl | 1-(3-dimethylaminopropyl)-3-ethylcarbodiimide hydrochloride |
| HOSu | N—hydroxysuccinimide |
| THF | tetrahydrofuran |
| DMSO | dimethysulfoxide |
| DMF | dimethylformamide |
| Z | benzyloxycarbonyl group |
| t-Boc | t-butyloxycarbonyl |

| Ac | acetyl. |

EXAMPLE 1

Preparation of N-benzyloxycarbonyl-alanyl-prolinal of the formula (1)

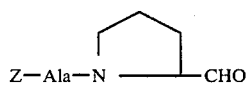

(1)

In 200 ml of THF was dissolved 22.3 g of N-benzyloxycarbonylalanine. To this solution were added under cooling with edible salt and ice 11.5 g of HOSu and 20.6 g of DCC, and the mixture was stirred for 21 hours at 4° C. The reaction liquid was filtered and the filtrate was evaporated until dryness whereby a semi-solid substance was obtained. This substance was recrystallized from isopropyl alcohol to obtain a white solid substance which was then dissolved in 470 ml of THF. To this solution was added 7.4 g of L-prolinol, and the mixture was stirred for 72 hours at room temperature. After removal of THF by distillation, the residue was dissolved in 300 ml of ethyl acetate and the solution was washed with 100 ml of 1-M $Na_2CO_3$ solution, dehydrated over anhydrous $Na_2SO_4$ and evaporated until dryness. To the resultant oily substance were added 32.4 g of WSCD.HCl and 180 ml of redistilled DMSO, and the mixture was stirred for 10 minutes. Subsequently, 6 ml of a DMSO solution of 2-M anhydrous $H_3PO_4$ was added and the whole was stirred for further 2 hours. The reaction was stopped with 360 ml of a buffer solution of 1-M potassium phosphate of pH 7.5. The reaction mixture was extracted with 250 ml of ethyl acetate, and the extract was dried over anhydrous $Na_2SO_4$. The ethyl acetate was distilled off and the residue was dissolved in 250 ml of ethanol. To this solution was added 200 g of $NaHSO_3$ in 350 ml of water, and the mixture was stirred vigorously for 10 minutes. After concentration of the ethanol up to about 350 ml, unreacted materials were removed twice with 100 ml of ether, and solid $Na_2CO_3$ was added until the pH value of the liquid became 9. After 5 minutes, the reaction liquid was extracted twice with 100 ml of ether, and the ether was then distilled off to leave an oily substance. Yield 2.9 g (9.9%).

Elementary analysis as $C_{16}H_{20}N_2O_4$: Calc. C 63.14; H 6.62; N 9.20. Found C 63.10; H 6.49; N 9.29.

EXAMPLE 2

Preparation of N-benzyloxycarbonyl-glycyl-prolinal of the formula (2)

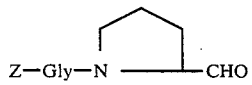

(2)

In 200 ml of THF was dissolved 17.7 g of N-benzyloxycarbonyl-glycin. To this solution were added under cooling with edible salt and ice 11.5 g of HOSu and 20.6 g of DCC, and the mixture was stirred for 21 hours at 4° C. The reaction liquid was filtered and the filtrate was evaporated whereby a semi-solid substance was obtained. This substance was recrystallized from isopropyl alcohol to obtain a white solid substance which was then dissolved in 600 ml of THF. To this solution was added 9.2 g of L-prolinol, and the mixture was stirred for 72 hours at room temperature. After removal of THF by distillation, the residue was dissolved in 300 ml of ethyl acetate and the solution was washed with 100 ml of a 1-M $Na_2CO_3$ solution, dehydrated with anhydrous $Na_2SO_4$ and evaporated until dryness. To the resultant oily substance were added 38.7 g of WSCD.HCl and 155 ml of redistilled DMSO, and the mixture was stirred for 10 minutes. Successively, 7.7 ml of a DMSO solution of 2-M anhydrous $H_3PO_4$ was added and the mixture was stirred for further 2 hours. The reaction was stopped with 360 ml of a buffer solution of 1-M potassium phosphate of pH 7.5. The reaction mixture was extracted with 250 ml of ethyl acetate, and the extract was dried over anhydrous $Na_2SO_4$. The ethyl acetate was distilled off and the residue was dissolved in 300 ml of ethanol. To this solution was added 200 g of $NaHSO_3$ in 350 ml of water, and the mixture was stirred vigorously for 10 minutes. After concentration of the ethanol up to about 350 ml, unreacted materials were eliminated twice with 100 ml of ether, and solid $Na_2CO_3$ was added until the pH value of the liquid became 9. After 5 minutes, the reaction liquid was extracted twice with 100 ml of ether, and the ether was then distilled off to leave an oily substance. Yield 4.5 g (15.6%).

EXAMPLE 3

Preparation of N-benzyloxycarbonyl-valyl-prolinal of the formula (3)

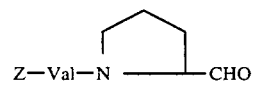

(3)

In 200 ml of THF was dissolved 22.1 g of N-benzyloxycarbonylvaline. To this solution were added under cooling with edible salt and ice 11.5 g of HOSu and 20.6 g of DCC, and the mixture was stirred for 21 hours at 4° C. The reaction liquid was filtered and the filtrate was evaporated whereby a semi-solid substance was obtained. This substance was recrystallized from isopropyl alcohol to obtain a white solid substance which was then dissolved in 470 ml of THF. To this solution was added 8.6 g of L-prolinol, and the mixture was stirred for 72 hours at room temperature. After removal of THF by distillation, the residue was dissolved in 300 ml of ethyl acetate and the solution was washed with 100 ml of 1-M $Na_2CO_3$, dehydrated with anhydrous $Na_2SO_4$ and evaporated until dryness. To the resultant oily substance were added 43.1 g of WSCD.HCl and 150 ml of redistilled DMSO, and the mixture was stirred for 10 minutes. Subsequently, 7 ml of a DMSO solution of 2-M anhydrous $H_3PO_4$ was added and the mixture was stirred for further 2 hours. The reaction was stopped with 300 ml of a buffer solution of 1-M potassium phosphate of pH 7.5. The reaction mixture was extracted with 200 ml of ethyl acetate, and the extract was dried over anhydrous $Na_2SO_4$. The ethyl acetate was distilled off and the residue was dissolved in 200 ml of ethanol. To this solution was added 200 g of $NaHSO_3$ in 350 ml of water, and the mixture was stirred vigorously for 10 minutes. After concentration of the ethanol up to about 350 ml, unreacted materials were eliminated twice with 100 ml of ether, and solid Na₂CO₃ was added until the pH value of the liquid became 9. After 5 minutes, the reaction liquid was extracted twice with 100 ml of ether, and the ether was then distilled off to leave an oily substance. Yield 5.7 g (17.2%).

Elementary analysis as $C_{18}H_{24}N_2O_4$: Calc. C 65.04; H 7.28; N 8.43. Found C 64.82; H 7.39; N 8.39.

EXAMPLE 4

Preparation of N-benzyloxycarbonyl-prolyl-prolinal of the formula (4):

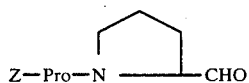

(4)

In 200 ml of THF was dissolved 22.1 g of N-benzyloxycarbonyl-proline. To this solution were added under cooling with edible salt and ice 11.5 g of HOSu and 20.6 g of DCC, and the mixture was stirred for 21 hours at 4° C. The reaction liquid was filtered and the filtrate was evaporated whereby a semi-solid substance was obtained. This substance was recrystallized from isopropyl alcohol to obtain a white solid substance which was then dissolved in 450 ml of THF. To this solution was added 8.2 g of L-prolinol, and the mixture was stirred for 72 hours at room temperature. After removal of THF by distillation, the residue was dissolved in 300 ml of ethyl acetate and the solution was washed with 100 ml of 1-M Na₂CO₃, dehydrated with anhydrous Na₂SO₄ and evaporated until dryness. To the resultant white solid substance were added 40.5 g of WSCD.HCl and 150 ml of redistilled DMSO, and the mixture was stirred for 10 minutes. Subsequently, 6.3 ml of a DMSO solution of 2-M anhydrous H₃PO₄ was added and the mixture was stirred for further 2 hours. The reaction was stopped with 350 ml of a buffer solution of 1-M potassium phosphate of pH 7.5. The reaction mixture was extracted with 200 ml of ethyl acetate, and the extract was dried over anhydrous Na₂SO₄. The ethyl acetate was distilled off and the residue was dissolved in 200 ml of ethanol. To this solution was added 200 g of NaHSO₃ in 350 ml of water, and the mixture was stirred vigorously for 10 minutes. After concentration of the ethanol up to about 350 ml, unreacted materials were eliminated twice with 100 ml of ether, and solid Na₂CO₃ was added until the pH value of the liquid became 9. After 5 minutes, the reaction liquid was extracted twice with 100 ml of ether, and the ether was then distilled off to leave an oily substance. Yield 3.4 g (10.3%).

Elementary analysis as $C_{18}H_{22}N_2O_4$: Calc. C 65.44; H 6.70; N 8.48. Found: C 65.28; H 6.83; N 8.59.

IR $\nu_{max}^{KBr}$ cm⁻¹: 2995, 2880, 1690, 1645, 1420, 1355, 1045.

EXAMPLE 5

Preparation of N-benzyloxycarbonyl-leucyl-prolinal of the formula (5):

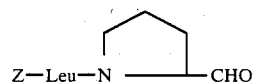

(5)

In 200 ml of THF was dissolved 26.5 g of N-benzyloxycarbonyl-leucin. To this solution were added under cooling with edible salt and ice 11.5 g of HOSu and 20.6 g of DCC, and the mixture was stirred for 21 hours at 4° C. The reaction liquid was filtered and the filtrate was evaporated whereby a semi-solid substance was obtained. This substance was recrystallized from isopropyl alcohol to obtain a white solid substance which was then dissolved in 400 ml of THF. To this solution was added 7.9 g of L-prolinol, and the mixture was stirred for 72 hours at room temperature. After removal of THF by distillation, the residue was dissolved in 300 ml of ethyl acetate and the solution was washed with 100 ml of 1-M Na₂CO₃, dehydrated with anhydrous Na₂SO₄ and evaporated until dryness. To the resultant oily substance were added 33.5 g of WSCD-HCl and 140 ml of redistilled DMSO, and the mixture was stirred for 10 minutes. Subsequently, 6.2 ml of a DMSO solution of 2-M anhydrous H₃PO₄ was added and the mixture was stirred for further 2 hours. The reaction was stopped with 300 ml of a buffer solution of 1-M potassium phosphate of pH 7.5. The reaction mixture was extracted with 300 ml of ethyl acetate, and the extract was dried over anhydrous Na₂SO₄. The ethyl acetate was distilled off and the residue was dissolved in 300 ml of ethanol. To this solution was added 200 g of NaHSO₃ in 350 ml of water, and the mixture was stirred vigorously for 10 minutes. After concentration of the ethanol up to about 350 ml, unreacted materials were eliminated twice with 100 ml of ether, and solid Na₂CO₃ was added until the pH value of the liquid became 9. After 5 minutes, the reaction liquid was extracted twice with 100 ml of ether, and the ether was then distilled off to leave an oily substance. Yield 4.2 g (12.1%).

EXAMPLE 6

Preparation of t-butyloxycarbonyl-alanyl-prolinal of the formula (6):

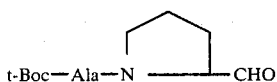

(6)

In 200 ml of THF was dissolved 22.1 g of t-butyloxycarbonylalanine. To this solution were added under cooling with edible salt and ice 11.5 g of HOSu and 20.6 g of DCC, and the mixture was stirred for 21 hours at 4° C. The reaction liquid was filtered and the filtrate was evaporated whereby a semi-solid substance was obtained. This substance was recrystallized from chloroform to obtain a white solid substance which was then dissolved in 400 ml of THF. To this solution was added 7.5 g of L-prolinol, and the mixture was stirred for 72 hours at room temperature. After removal of THF by distillation, the residue was dissolved in 300 ml of ethyl acetate and the solution was washed with 100 ml of 1-M Na₂CO₃, dehydrated with anhydrous Na₂SO₄ and evaporated until dryness. To the resultant oily substance were added 32.5 g of WSCD.HCl and 130 ml of redistilled DMSO, and the mixture was stirred for 10 minutes. Subsequently, 6 ml of DMSO solution of 2-M anhydrous H₃PO₄ was added and the mixture was stirred for further 2 hours. The reaction was stopped with 300 ml of a buffer solution of 1-M potassium phosphate of pH 7.5. The reaction mixture was extracted with 250 ml of ethyl acetate, and the extract was dried over anhydrous Na₂SO₄. The ethyl acetate was distilled off and the residue was dissolved in 250 ml of ethanol.

To this solution was added 200 g of NaHSO$_3$ in 350 ml of water, and the mixture was stirred vigorously for 10 minutes. After concentration of the ethanol up to about 350 ml, unreacted materials were eliminated twice with 100 ml of ether, and solid Na$_2$CO$_3$ was added until the pH value of the liquid became 9. After 5 minutes, the reaction liquid was extracted twice with 100 ml of ether, and the ether was then distilled off to leave an oily substance. Yield 1.2 g (4.5%).

Elementary analysis as C$_{13}$H$_{22}$O$_4$N$_2$: Calc. C 57.76; H 8.20; N 10.36. Found: C 57.81; H 8.30; N 10.22.

EXAMPLE 7

Preparation of t-butyloxycarbonyl-phenylalanyl-prolinal of the formula (7):

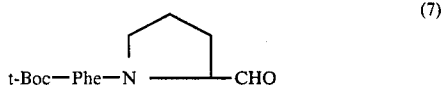

(7)

In 200 ml of THF was dissolved 29.9 g of t-butyloxycarbonyl-phenylalanine. To this solution were added under cooling with edible salt and ice 11.5 g of HOSu and 20.6 g of DCC, and the mixture was stirred for 21 hours at 4° C. The reaction liquid was filtered and the filtrate was evaporated whereby a semi-solid substance was obtained. This substance was recrystallized from chloroform to obtain a white solid substance which was then dissolved in 400 ml of THF. To this solution was added 7.4 g of L-prolinol, and the mixture was stirred for 72 hours at room temperature. After removal of THF by distillation, the residue was dissolved in 300 ml of ethyl acetate and the solution was washed with 100 ml of 1-M Na$_2$CO$_3$, dehydrated with anhydrous Na$_2$SO$_4$ and evaporated until dryness. To the resultant oily substance were added 29.2 g of WSCD.HCl and 120 ml of redistilled DMSO, and the mixture was stirred for 10 minutes. Subsequently, 5.8 ml of a DMSO solution of 2-M anhydrous H$_3$PO$_4$ was added and the mixture was stirred for further 2 hours. The reaction was stopped with 300 ml of a buffer solution of 1-M potassium phosphate of pH 7.5. The reaction mixture was extracted with 250 ml of ethyl acetate, and the extract was dried over anhydrous Na$_2$SO$_4$. The ethyl acetate was distilled off and the residue was dissolved in 250 ml of ethanol. To this solution was added 200 g of NaHSO$_3$ in 350 ml of water, and the mixture was stirred vigorously for 10 minutes. After concentration of the ethanol up to about 350 ml, unreacted materials were eliminated twice with 100 ml of ether, and solid Na$_2$CO$_3$ was added until the pH value of the liquid became 9. After 5 minutes, the reaction liquid was extracted twice with 100 ml of ether, and the ether was then distilled off to leave an oily substance. Yield 3.3 g (8.4%).

EXAMPLE 8

Preparation of t-butyloxycarbonyl-seryl-prolinal of the formula (8):

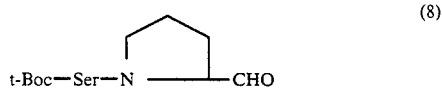

(8)

In 200 ml of THF was dissolved 20.5 g of t-butyloxycarbonylserine. To this solution were added under cooling with edible salt and ice 11.5 g of HOSu and 20.6 g of DCC, and the mixture was stirred for 21 hours at 4° C. The reaction liquid was filtered and the filtrate was evaporated whereby a semi-solid substance was obtained. This substance was recrystallized from chloroform to obtain a white solid substance which was then dissolved in 450 ml of THF. To this solution was added 18.0 g of L-prolinol, and the mixture was stirred for 72 hours at room temperature. After removal of THF by distillation, the residue was dissolved in 330 ml of ethyl acetate and the solution was washed with 100 ml of 1-M Na$_2$CO$_3$, dehydrated with anhydrous Na$_2$SO$_4$ and evaporated until dryness. To the resultant oily substance were added 36.9 g of WSCD.HCl and 150 ml of redistilled DMSO, and the mixture was stirred for 10 minutes. Subsequently, 6.5 ml of a DMSO solution of 2-M anhydrous H$_3$PO$_4$ was added and the mixture was stirred for further 2 hours. The reaction was stopped with 300 ml of a buffer solution of 1-M potassium phosphate of pH 7.5. The reaction mixture was extracted with 300 ml of ethyl acetate, and the extract was dried over anhydrous Na$_2$SO$_4$. The ethyl acetate was distilled off and the residue was dissolved in 250 ml of ethanol. To this solution was added 200 g of NaHSO$_3$ in 350 ml of water, and the mixture was stirred vigorously for 10 minutes. After concentration of the ethanol up to about 350 ml, unreacted materials were eliminated twice with 100 ml of ether, and solid Na$_2$CO$_3$ was added until the pH value of the liquid became 9. After 5 minutes, the reaction liquid was extracted twice with 100 ml of ether, and the ether was then distilled off to leave an oily substance. Yield 2.1 g (7.3%).

EXAMPLE 9

Preparation of t-butyloxycarbonyl-tyrosyl-prolinal of the formula (9):

(9)

In 200 ml of THF was dissolved 28.1 g of t-butyloxycarbonyltyrosine. To this solution were added under cooling with edible salt and ice 11.5 g of HOSu and 20.6 of DCC, and the mixture was stirred for 21 hours at 4° C. The reaction liquid was filtered and the filtrate was evaporated whereby a semi-solid substance was obtained. This substance was recrystallized from chloroform to obtain a white solid substance which was then dissolved in 500 ml of THF. To this solution was added 6.0 g of L-prolinol, and the mixture was stirred for 72 hours at room temperature. After removal of THF by distillation, the residue was dissolved in 200 ml of ethyl acetate and the solution was washed with 100 ml of 1-M Na$_2$CO$_3$, dehydrated with anhydrous Na$_2$SO$_4$ and evaporated until dryness. To the resultant oily substance were added 20.3 g of WSCD.HCl and 90 ml of redistilled DMSO, and the mixture was stirred for 10 minutes. Subsequently, 3.9 ml of a DMSO solution of 2-M anhydrous H$_3$PO$_4$ was added and the mixture was stirred for further 2 hours. The reaction was stopped with 300 ml of a buffer solution of 1-M potassium phosphate of pH 7.5. The reaction mixture was extracted with 200 ml of ethyl acetate, and the extract was dried over anhydrous Na$_2$SO$_4$. The ethyl acetate was distilled off and the residue was dissolved in 200 ml of ethanol. To this solution was added 200 g of NaHSO$_3$ in 350 ml of water, and the mixture was stirred vigorously for 10 minutes. After concentration of the ethanol up to about 350 ml, unreacted materials were eliminated twice with 100 ml of ether, and solid Na$_2$CO$_3$ was added until the pH value of the liquid became 9. After 5 minutes, the reaction liquid was extracted twice with 100 ml of ether, and the ether was then distilled off to leave an oily substance. Yield 0.8 g (2.2%).

EXAMPLE 10

Preparation of acetyl-glycyl-prolinal of the formula (10):

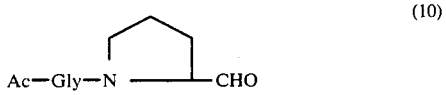

(10)

In 150 ml of THF was dissolved 11.7 g of acetyl-glycin. To this solution were added 11.5 g of HOSu and 20.6 g of DCC, and the mixture was stirred for 21 hours at 4° C. The reaction liquid was filtered and the filtrate was evaporated under reduced pressure whereby a semi-solid substance was obtained. This substance was recrystallized from chloroform to obtain a white solid substance which was then dissolved in 350 ml of THF. To this solution was added 4.2 g of L-prolinol, and the mixture was stirred for 72 hours at room temperature. After removal of THF by distillation, the residue was dissolved in 200 ml of ethyl acetate and the solution was washed with 100 ml of 1-M Na$_2$CO$_3$, dehydrated with anhydrous Na$_2$SO$_4$ and evaporated until dryness. To the resultant oily substance were added 18.6 g of WSCD.HCl and 75 ml of redistilled DMSO, and the mixture was stirred for 10 minutes. Subsequently, 3.2 ml of a DMSO solution of 2-M anhydrous H$_3$PO$_4$ was added and the mixture was stirred for further 2 hours. The reaction was stopped with 160 ml of a buffer solution of 1-M potassium phosphate of pH 7.5. The reaction mixture was extracted with 150 ml of ethyl acetate, and the extract was dried over anhydrous Na$_2$SO$_4$. The ethyl acetate was distilled off and the residue was dissolved in 100 ml of ethanol. To this solution was added 50 g of NaHOS$_3$ in 90 ml of water, and the mixture was stirred vigorously for 10 minutes. After concentration of the ethanol up to about 90 ml, unreacted materials were eliminated twice with 60 ml of ether, and solid Na$_2$CO$_3$ was added until the pH value of the liquid became 9. After 5 minutes, the reaction liquid was extracted twice with 60 ml of ether, and the ether was then distilled off to leave an oily substance. Yield 0.3 g (1.5%).

EXAMPLE 11

Preparation of acetyl-prolyl-prolinal of the formula (11):

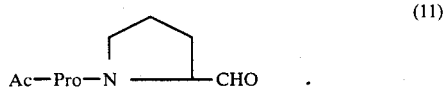

(11)

In 200 ml of THF was dissolved 15.7 g of acetyl-proline. To this solution were added under cooling with edible salt and ice 11.5 g of HOSu and 20.6 g of DCC, and the mixture was stirred for 21 hours at 4° C. The reaction liquid was filtered and the filtrate was evaporated whereby a semi-solid substance was obtained. This substance was recrystallized from isopropyl alcohol to obtain a white solid substance which was then dissolved in 400 ml of THF. To this solution was added 7.5 g of L-prolinol, and the mixture was stirred for 72 hours at room temperature. After removal of THF by distillation, the residue was dissolved in 300 ml of ethyl acetate and the solution was washed with 100 ml of 1-M Na$_2$CO$_3$, dehydrated with anhydrous Na$_2$SO$_4$ and evaporated until dryness. To the resultant oily substance were added 35.8 g of WBCD.HCl and 160 ml of redistilled DMSO, and the mixture was stirred for 10 minutes. Subsequently, 7.1 ml of a DMSO solution of 2-M anhydrous H$_3$PO$_4$ was added and the mixture was stirred for further 2 hours. The reaction was stopped with 300 ml of a buffer solution of 1-M potassium phosphate of pH 7.5. The reaction mixture was extracted with 350 ml of ethyl acetate, and the extract was dried over anhydrous Na$_2$SO$_4$. The ethyl acetate was distilled off and the residue was dissolved in 300 ml of ethanol. To this solution was added 200 g of NaHSO$_3$ in 350 ml of water, and the mixture was stirred vigorously for 10 minutes. After concentration of the ethanol up to about 300 ml, unreacted materials were eliminated twice with 100 ml of ether, and solid Na$_2$CO$_3$ was added until the pH value of the liquid became 9. After 5 minutes, the reaction liquid was extracted twice with 100 ml of ether, and the ether was then distilled off to leave an oily substance. Yield 5.5 g (23.5%).

Elementary analysis as $C_{12}H_{19}N_2O_3$: Calc. C 56.44; H 7.50; N 10.97. Found: C 56.28; H 7.54; N 10.86.

The following examples illustrate the preparation of the antiamnestic agents of the present invention. It is to be construed, however, that the preparation of the antiamnestic agents of the present invention is not limited to these examples.

EXAMPLE A

Injection preparations (1) Recipe

| | |
|---|---|
| N—Benzyloxycarbonyl-glycyl-L-prolinal | 10 mg |
| Hardened castor oil polyoxyethylene 60 mol ether | 40 mg |
| sorbitan monostearate | 2 mg |
| Propylene glycol | 60 mg |
| Refined soybean lecitin | 2 mg |
| Cholesterol | 1 mg |
| Dextrose | 50 mg |
| Distilled water to make | 1 ml |

(2) Preparation

N-Benzyloxycarbonyl-glycyl-L-prolinal, hardened castor oil polyoxyethylene 60 mol ether, sorbitan monostearate, propylene glycol, refined soybean lacitin and cholesterol are mixed and fused to form a homogeneous liquid in a water bath heated at about 80° C. To this liquid is added with stirring distilled water heated at about 80° C. to form a solubilized homogeneous system. Dextrose is then added and distilled water is added to make the volume to 1 ml. The liquid is subjected to sterilizing filtration, and charged into an amber ampoule which is then sealed.

EXAMPLE B

Soft capsulated preparations (1) Recipe

| | |
|---|---|
| t-Butyloxycarbonyl-L-alanyl-prolinal | 20 mg |

| | |
|---|---|
| Macrogol 400 | 350 mg |
| Propylene glycol | 38 mg |
| Dipotassium glycyrrhizinate | 1 mg |
| Menthol oil | 1 mg |
| Gelatin | 122 mg |
| Glycerol | 30.5 mg |
| D-Sorbitol liquid | 12.2 mg |
| Ethyl p-hydroxybenzoate | 0.8 mg |
| Propyl p-hydroxybenzoate | 0.5 mg |

(2) Preparation t-Butyloxycarbonyl-L-alanyl-prolinal, Macrogol 400, dipotassium glycyrrhizimate, menthol oil and propylene glycol are homogeneously blended to form a suspension. Separately, a coating agent for soft capsules is manufactured from gelatin, glycerol, D-sorbitol liquid, ethyl p-hydroxybenzoate and propyl p-hydroxybenzoate. Using the suspension and the coating agent, a soft capsule is prepared.

It is understood that the preceding representative examples may be varied within the scope of the present specification both as to reactants, reaction conditions and ingredients to be blended, by one skilled in the art to achieve essentially the same results.

As many widely different embodiments of this invention may be made without departing from the spirit and scope thereof, it is to be construed that this invention is not limited to the specific embodiments thereof except as defined in the appended claims.

What is claimed is:

1. A method for treating a memory disorder comprising administering to a patient an effective amount of at least one prolinal derivative of the formula

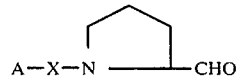

wherein A is an amino protecting group selected from the group consisting of N-benzyloxycarbonyl, t-butyloxycarbonyl and $C_{2-4}$ acyl and X is a member selected from the group consisting of alanine, glycine, phenylalanine, proline, valine, leucine, serine and tyrosine.

2. A method according to claim 1, wherein said prolinal derivative is orally administered in an amount of between 1 and 900 mg/kg of body weight in terms of daily dose.

3. A method according to claim 1, wherein said prolinal derivative is intravenously injected in an amount of between 0.5 and 500 mg/kg of body weight in terms of daily dose.

4. A method according to claim 1, wherein A is a member selected from the group consisting of N-benzyloxycarbonyl, t-butyloxycarbonyl, and acetyl.

5. A method according to claim 4, wherein said prolinal derivative is orally administered in an amount of between 1 and 900 mg/kg of body weight in terms of daily dose.

6. A method according to claim 4, wherein said prolinal derivative is intraveneously injected in an amount of between 0.5 and 500 mg/kg of body weight in terms of daily dose.

* * * * *